US007045367B2

(12) United States Patent
Kaganove et al.

(10) Patent No.: US 7,045,367 B2
(45) Date of Patent: May 16, 2006

(54) NANO-SCALED DENDRIMER-BASED COLORIMETRIC BIOSENSORS

(75) Inventors: Steven N. Kaganove, Midland, MI (US); Petar R. Dvornic, Midland, MI (US)

(73) Assignee: Michigan Molecular Institute, Midland, MI (US)

( * ) Notice: Subject to any disclaimer, the term of this patent is extended or adjusted under 35 U.S.C. 154(b) by 331 days.

(21) Appl. No.: 10/068,378

(22) Filed: Feb. 6, 2002

(65) Prior Publication Data

US 2002/0192843 A1 Dec. 19, 2002

Related U.S. Application Data

(60) Provisional application No. 60/278,307, filed on Mar. 23, 2001.

(51) Int. Cl.
*G01N 33/547* (2006.01)
*G01N 33/532* (2006.01)
*G01N 21/63* (2006.01)
*G01N 21/78* (2006.01)

(52) U.S. Cl. .................. 436/532; 435/6; 436/164; 436/172; 436/531; 436/546; 436/805; 436/501

(58) Field of Classification Search .............. 436/546, 436/531, 532, 501, 164, 172, 805; 435/6
See application file for complete search history.

(56) References Cited

U.S. PATENT DOCUMENTS

| 5,622,872 A | 4/1997 | Ribi |
| 6,001,556 A | 12/1999 | Charych et al. |
| 6,022,748 A | 2/2000 | Charych et al. |

OTHER PUBLICATIONS

Sui, G., Micic, M., Huo, Q., Leblanc, R. M.; "Studies of a Novel Polymerizable Amphiphilic Dendrimer" *Colloids and Surfaces A: Physicochemical and Engineering Aspects*, 171 (2000) pp. 185-197.
Balogh L. et al., "Architectural Copolymers of PAMSAM Dendrimers and Ionic Polyacetylenes," *Macromolecules*, vol. 32, No. 4, Feb. 23, 1999, pp. 1036-1042.

*Primary Examiner*—Mary E. Ceperley
(74) *Attorney, Agent, or Firm*—Price, Heneveld, Cooper, DeWitt & Litton, LLP

(57) ABSTRACT

Molecular chemical and/or biological sensors that exhibit a very high density of sensing functionality and which are applicable to a wide variety of different analytes, and enable rapid, convenient and economical detection of analytes are prepared by reacting a dendritic polymer with a diacetylene reagent wherein the diacetylene functional groups are subsequently intramolecularly polymerized to form segments having alternating conjugated double and triple bonds. Sensory groups that can bind with an analyte are bonded to the acetylene monomer units to form molecular sensors that produce observable and measurable color changes when an analyte binds with the sensory groups.

7 Claims, 2 Drawing Sheets

NANO-SCALED DENDRIMER-BASED COLORIMETRIC BIOSENSORS

CROSS-REFERENCE TO RELATED APPLICATION

This application claims priority under 35 U.S.C. § 119(e) on U.S. Provisional Application No. 60/278,307 entitled NANO-SCALED DENDRIMER-BASED COLORIMETRIC BIOSENSORS, filed Mar. 23, 2001, the entire disclosure of which is incorporated herein by reference.

FIELD OF THE INVENTION

This invention relates to a composition of matter that is useful for detecting chemical or biological analytes, and methods of this detection.

BACKGROUND OF THE INVENTION

There has been a well recognized need for fast, reliable and inexpensive analytical techniques for detecting the presence of chemical and/or biological analytes, and/or quantifying the amount of chemical and/or biological analytes present in a sample. Conventional analytical chemistry techniques, such as chromatographic techniques, mass spectrometry, titration, etc. can provide reliable results. However, these conventional analytical techniques are generally time consuming and expensive. Further, they are generally performed in a laboratory at a fixed location, and are not easily portable or adaptable for portable use.

Chemical and/or biological sensors have been developed to overcome some of the disadvantages with conventional analyte detection techniques. The known chemical and/or biological sensors are generally composed of two distinct functional components: a sensing element and a transducer. The sensing element chemically interacts with the analyte of interest to induce changes in some detectable physicochemical property, and the transducer detects these physicochemical property changes and converts them into a measurable output signal.

Most chemical and/or biological sensors can be categorized as optical, resistive, electrochemical or acoustic mass sensing devices. Often complex instruments, such as high-resolution charge-coupled devices (CCDs) with optical fiber sensors or electronic oscillating circuitry with surface acoustic wave (SAW) mass sensors, are required to operate known chemical and/or biochemical sensors. Preferred for chemical and/or biological sensors are optical devices that rely on calorimetric, fluorimetric or fluorescence depolarization sensors, wherein the molecular recognition event triggers a drastic color change that is observable by the naked eye and/or is quantifiable by optical absorption using spectroscopic instrumentation. A particularly promising step in this direction is a recently disclosed system of conjugated polymer vesicles that are bonded together with a polydiacetylene (PDA) backbone. When conjugated to biologically interactive carbohydrates such as sialic acid and ganglioside $G_{M1}$, the resulting highly colored polymerized v change in the presence of influenza virus and cholera toxin, respectively. Such color changes result from perturbation of PDA structural conformation and the extent of uninterrupted conjugation, which is typically caused by heat, organic solvents, changes in pH, or mechanical stress.

Among the various classes of well known polymerizable organic functional groups, diacetylenes are rather unusual in that a highly ordered state is required for their polymerization to occur. In practice, polymerization has been achieved when diacetylene monomers are locked in solid state conformations such as crystal lattices, Langmuir-Blodgett (LB) films, self-assembled monolayers (SAM) or vesicles, thereby allowing polymerization to proceed by repeated 1,4-addition of the diacetylene monomers. This type of geometrically constrained polymerization reaction (illustrated in FIG. 1) is referred to as a "topochemical polymerization," and it is typically initiated by heat or irradiation from an ultraviolet or gamma radiation source. The resulting polymers have highly conjugated segments, composed of alternating conjugated double and triple bonds along the backbone, and as a consequence of this conjugation they are usually highly colored. For example, in the case of polymerized vesicles the predominant colors are blue, red or violet.

However, the reported PDA vesicle system has significant limitations. First, since vesicle formation is based on self-assembly at the molecular level, it does not offer direct control of molecular architecture, resulting in a variety of different sizes and shapes when lipids randomly self-assemble into vesicles. Secondly, although polymerized lipids are dispersible in aqueous media, they are not truly soluble, and therefore lack the kinetic and thermodynamic advantages that a truly homogenous assay would offer.

SUMMARY OF THE INVENTION

The present invention overcomes deficiencies of the known chemical and/or biological sensors by combining the colorimetric ability of polydiacetylene reporting units with the soluble polymer architectures and controllable sizes and shapes of dendritic polymers (e.g., hyperbranched polymers, dendrimers, and the like). The sensors of this invention exhibit a very high density of sensing functionality, are applicable to a wide variety of different analytes, and enable more rapid, convenient and economical detection. These attributes are particularly important in the biomedical field, food processing industries, toxicology, environmental protection and similar health related fields.

The chemical and/or biological sensors of this invention are based on a dendritic polymer core having intramolecular segments of alternating conjugated double and triple bonds.

In one aspect of the invention, these macromolecular compounds having a dendritic polymer core and intramolecular segments of alternating conjugated double and triple bonds are attached to one or more sensory ligands capable of binding to one or more analytes.

In another embodiment, to a dendritic polymer core is attached a heterogeneous mixture of end groups, at least one of which is comprised of two conjugated triple bonds (diacetylenic moiety) and at least one of which does not contain two conjugated triple bonds, such as a saturated hydrocarbon functional group.

These and other features, advantages and objects of the present invention will be further understood and appreciated by those skilled in the art by reference to the following specification and claims.

DESCRIPTION OF THE PREFERRED EMBODIMENTS

Figure 1:
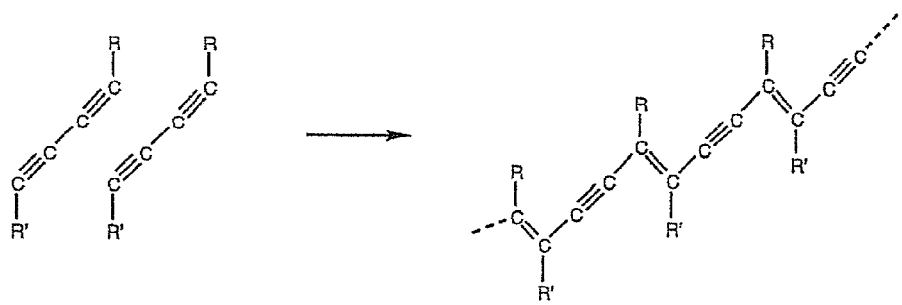
FIG. 1 is a schematic representation of diacetylene topochemical polymerization.

The novel macromolecular compounds of this invention, which comprise a dendritic polymer core and intramolecular segments of alternating conjugated double and triple bonds, are useful for preparing chemical and/or biological sensors by bonding one or more chemical and/or biological sensory ligands to terminal functional groups located at the surface of the macromolecular compound. The macromolecular compounds of this invention may also have utility in other applications such as in drug delivery and in plastic structural components that change color as a function of stress and/or physical fatigue.

Other macromolecular compounds covered by this invention include those where a dendritic polymer core is attached to a heterogeneous mixture of end groups, at least one of which is comprised of two conjugated triple bonds (diacetylenic moiety) and at least one of which does not contain two conjugated triple bonds, such as a saturated hydrocarbon functional group. Chemical and/or biological sensors may be prepared by bonding one or more chemical and/or biological sensory ligands to terminal functional groups located at the surface of this macromolecular compound. Macromolecular compounds in which up to 100% of dendritic polymer core end groups are attached to lipids containing two conjugated triple bonds may be included in this invention provided that one or more chemical and/or biological ligands are also attached to the ends of these lipids.

The colorimetric macromolecules of this invention are prepared by reacting a dendritic polymer molecule having terminal functional groups with a potentially calorimetric reagent which contains functional groups that can be intramolecularly polymerized to form segments having alternating conjugated double and triple bonds. These macromolecules may also exhibit photoluminescent properties before and/or after intramolecular polymerization. Even a macromolecule containing a single segment with two conjugated triple bonds may exhibit significant photoluminescent activity. An advantage of using a dendritic polymer core is that the resulting colorimetric or photoluminescent macromolecules can be made soluble in a variety of solvents such as water or hydrophobic organic solvents, depending on the selection of the dendritic polymer core, selection of the terminal functional groups and/or modification of the terminal functional groups, and the characteristics and the molecular density of potentially colorimetric reagent bonded to the dendritic core. Another advantage of using a dendritic polymer core is that it allows high intramolecular density of sensory and/or reporter functionalities such that interactions between these functionalities can be easily accomplished and/or intensified.

Suitable dendritic polymers which may be used include generally any of the known dendritic architectures including dendrimers, tecto-dendrimers, regular dendrons, dendrigrafts, and hyperbranched polymers. Dendritic star-branched polymers having a plurality of arms emanating from a nucleus may also be used. Accordingly, as used herein, dendritic polymers are polymers with densely branched structures having a large number of terminal reactive groups. A dendritic polymer includes several layers or generations of repeating units, usually referred to as branch cells, which all contain one or more branch points.

Dendritic polymers, including dendrimers and hyperbranched polymers, are prepared by reaction of monomeric units having two or more reactive groups, or a combination of monomeric units in which at least one of the monomeric units has at least three reactive groups. The dendrimers which can be used include those comprised of a plurality of dendrons that emanate from a common core which can be a single atom or a group of atoms. Each dendron generally consists of terminal surface groups, interior branch junctures having branching functionalities greater than or equal to two, and divalent connectors that covalently connect neighboring branching junctures.

Dendrons and dendrimers can be prepared by convergent or divergent synthesis. Divergent synthesis of dendrons and dendrimers involves a molecular growth process which occurs through a consecutive series of geometrically progressive step-wise additions of branches upon branches in a radially outward molecular direction to produce an ordered arrangement of layered branched cells. Each dendritic macromolecule includes a core cell, one or more layers of interior cells, and an outer layer of surface cells, wherein each of the cells includes a single branch juncture. The cells can be the same or different in chemical structure and branching functionality. The surface branch cells may contain either chemically reactive or passive functional groups. Chemically reactive surface groups can be used for further extension of dendritic growth or for modification of dendritic molecular surfaces. The chemically passive groups may be used to physically modify dendritic surfaces, such as to adjust the ratio of hydrophobic to hydrophilic terminals, and/or to improve the solubility of the dendritic polymer in a particular solvent.

Convergent synthesis of dendrimers and dendrons involves a growth process which begins from what will become the surface of the dendron or dendrimer and progresses in a radial molecular direction toward a focal point or core. In the case of dendrimers, it always ends with an anchoring reaction in which two or more dendrons are connected through their reactive focal points with an anchoring reagent. The dendritic polymers may be ideal or non-ideal, i.e., imperfect or defective. Imperfections are normally a cansequence of either incomplete chemical reactions, or competing side reactions. In practice, real dendritic polymers are generally non-ideal, i.e., they contain structural imperfections, which cause the appearance of molecular size distribution.

Hyperbranched polymers represent a class of dendritic polymers which contain higher levels of non-ideal irregular branching as compared to the generally more regular structure of dendrons and dendrimers. Specifically, hyperbranched polymers contain a relatively high number of irregular branches in which not every repeat unit contains a branch juncture. Hence, hyperbranched polymers contain a mixture of linear and fully branched repeating units, whereas an ideal dendrimer contains only fully branched repeating units, and an ideal linear polymer contains only linear repeating units.

The average degree of branching ($\overline{DB}$) may be defined as the number average fraction of branching groups per molecule, i.e., as the ratio of terminal groups plus branch groups to the total number of terminal groups, branch groups, and linear groups as follows:

$$\overline{DB} = \frac{N_t + N_b}{N_t + N_b + N_l}$$

where $N_t$ represents the number of terminal units, $N_b$ represents the number of branched units, and $N_l$ represents the number of linear units. For ideal dendrons and dendrimers this degree of branching is one; for ideal linear polymers it is zero; while for hyperbranched polymers it is greater than zero and less than one, with typical values ranging from about 0.25 to about 0.45.

Dendritic polymers suitable for use with this invention also include macromolecules commonly referred to as cascade molecules, arborols, arborescent grafted molecules, and the like.

They also include hypercomb-branched polymers that comprise non-cross-linked poly-branched polymers prepared by (1) forming a first set of linear polymer branches by initiating polymerization of a first set of monomers which are either protected against or non-reactive to branching and grafting during polymerization, each of the branches having a reactive end group upon completion of polymerization, the reactive end units being incapable of reacting with each other; (2) grafting the branches to a core molecule or core polymer having a plurality of reactive sites capable or reacting with the reactive end groups on the branches; (3) either deprotecting or activating a plurality of monomeric units on each of the branches to create reactive sites; (4) separately forming a second set of linear polymer branches by repeating step (1) with a second set of monomers; (5) attaching the second set of branches to the first set of branches by reacting the reactive end group of the second set of branches with the reactive sites on the first set of branches; and then repeating steps (3), (4) and (5) to add one or more subsequent set of branches.

For purposes of clarifying terminology it should be noted that dendrimers are synthesized by reiterative terminal branching, while hypercomb-branched polymers are synthesized by reiterative comb-branching. In dendrimers, subsequent generations or branches are attached to the terminal moieties of a previous generation, thus limiting the degree of branching to the functionality of the previous generation terminal moiety, which would typically be two or three. In contrast, by branching oligomers upon prior generation oligomer branches, hypercomb-branched polymers having a degree of branching which increases or varies from one generation to the next is possible.

Other suitable classes of dendritic polymers include various combinations of linked dendrimers, such as bridged dendritic polymers and/or dendritic polymer clusters wherein two or more dendritic polymer molecules are covalently bonded together through their reactive terminal groups (either directly or through a linking molecule such as an alpha,omega-telechelic linear oligomer/polymer or other difunctional or polyfunctional molecule), dendritic polymer chains, dendritic polymer networks (e.g., cross-linked dendritic polymers, and core-shell tecto-dendrimers (i.e., a composition comprising a single dendritic core polymer surrounded by a plurality of dendritic shell polymer molecules, each of which is chemically bonded to the surface of the core polymer molecule), or as pendant groups attached to a linear polymer (possibly conjugated).

Methods of preparing and characterizing dendrimers, dendrons, hyperbranched polymers, star-branched polymers, dense star-branched polymers and hypercomb-branched polymers are all well known in the art and thoroughly described in the literature.

Specific examples of dendritic polymers that may be used include polyamidoamine (PAMAM) dendrimers, dendrigrafts and hyperbranched polymers; poly(benzylether) dendrimers, dendrigrafts and hyperbranched polymers; polyester dendrimers and hyperbranched polymers; poly (propyleneimine) (PPI) dendrimers, dendrigrafts and hyperbranched polymers; organosilicon-containing dendrimers, dendrigrafts and hyperbranched polymers, polystyrene arborescent polymers, etc.

Generally, any dendritic polymer (i.e., any polymer having branches upon branches) may be used with this invention, with selection depending on factors such as cost, availability, solubility, and terminal functional group reactivity and density. Obviously, lower cost materials and commercially available materials are preferred when other factors such as solubility, terminal functional group reactivity and density are equal. Solubility may or may not be an important factor, depending upon the particular application in which the macromolecular compounds of this invention are used. However, in many cases, it may be desirable to use a dendritic polymer that is soluble in water, oil, or a particular solvent. In general, to provide the highest degree of sensor sensitivity, as manifested by an observable color change upon contact with a medium containing an analyte, dendritic polymers with a high density of sensing functionality are preferred. In general, this means that dendritic polymers having a high density of terminal functional groups are preferred for preparing the colorimetric macromolecules of this invention.

Examples of terminal functional groups that may be present on the dendritic polymer used for preparing the colorimetric macromolecules of this invention include hydroxy, mercapto, carboxyl, ester, alkoxy, alkenyl, allyl, vinyl, amino, halo, urea, oxiranyl, aziridinyl, oxazolinyl, imidazolinyl, sulfonato, phosphonato, hydrosilyl, isocyanato, isothiocyanato, etc. Various known chemistries are useable with these and other surface functional groups for attachment of the colorimetric reagent to the dendritic polymer core.

The colorimetric reagent may comprise any compound or compounds that can be covalently bonded to the terminal functional groups of the dendritic polymer molecule and subsequently reacted to form intramolecular and/or intermolecular segments containing alternating conjugated double and triple bonds, i.e., —C=C—C≡C— repeating units. Examples include diacetylenes such as 5,7-docosadiynoic acid, 10,12-pentacosadiynoic acid, 5,7-pentacosadiynoic acid, and combinations thereof. A variety of diacetylenic lipids are commercially available, but they can also be synthesized using the well known Cadiot-Chodkiewicz acetylene coupling reaction.

If the above mentioned diacetylenes do not undergo topochemical polymerization reaction, they may exhibit photoluminescent activity in their own right, which makes them suitable for potential detection of chemical and/or biological analytes. The diacetylene compounds may include only one terminal functional group that is reactive with a terminal functional group on the dendritic polymer. However, the diacetylene compounds used for preparing the colorimetric chemical and/or biological sensors of this invention have two terminal functional groups at opposite ends of the diacetylene reagent, one selected to react with the terminal functional groups of the dendritic polymer, and another that binds to a ligand sensory group.

Figure 2:
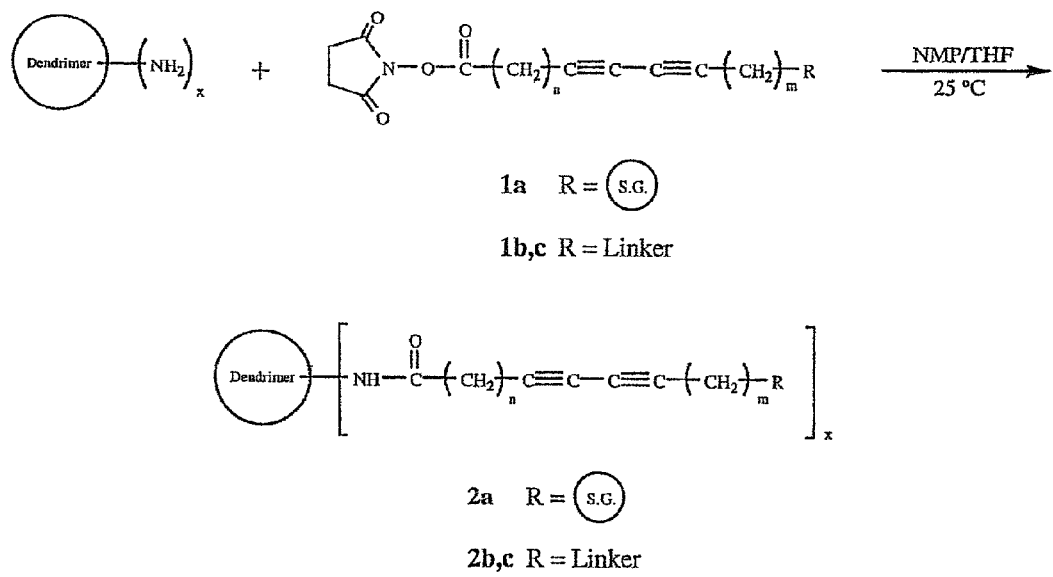
FIGS. 2 and 3 are schematic representations of pathways for synthesizing a particular class of chemical and/or biological sensors according to this invention.
Figure 3:
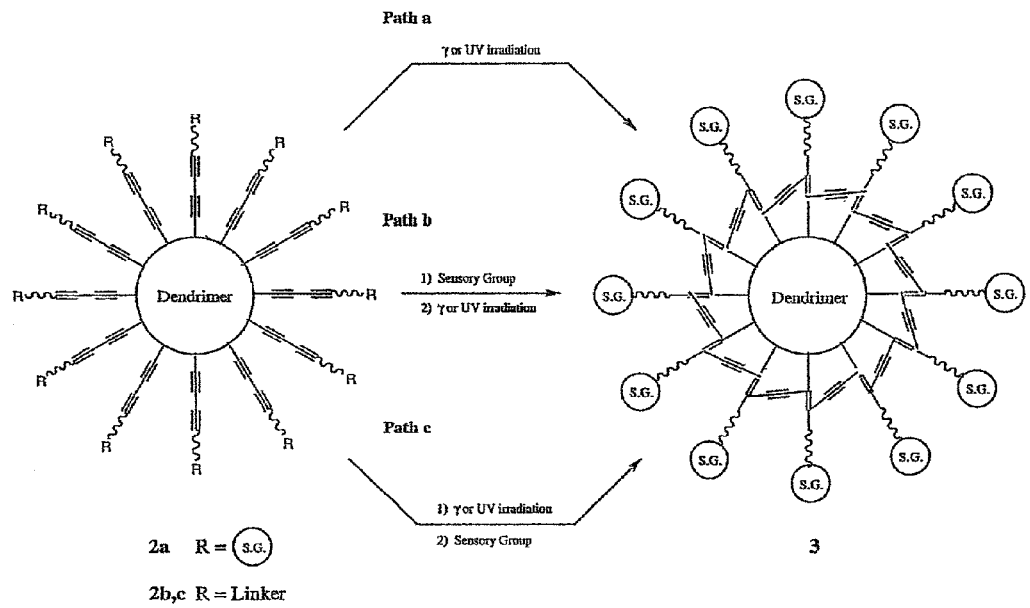
Figure 4:
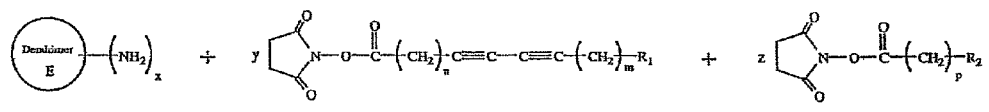
FIG. 4 is a schematic representation of pathways for synthesizing another class of chemical and/or biological sensors according to this invention.
Figure 4:
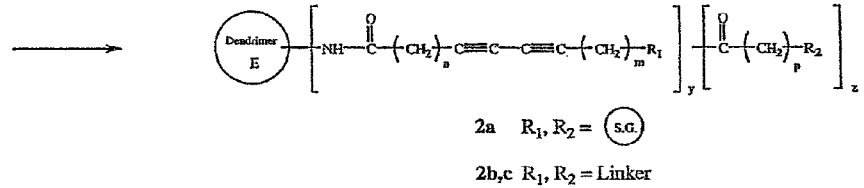

Preparation of a calorimetric chemical and/or biological sensor from an amine-terminated dendrimer and a succinimidyl-terminated diacetylene schematically in FIGS. 2, 3 and 4. In FIG. 2, a dendrimer having x terminal amine groups is reacted with a diacetylene reagent to form a dendrimer having x diacetylene terminal moieties that branch out radially from the dendrimer core. The resulting diacetylene-functionalized dendrimer can be converted into a calorimetric chemical and/or biological sensor by one of the synthetic pathways shown in FIG. 3. In path (a), sensory groups (designated "S.G.") are preattached to the diacetylenic lipid before being reacted with the dendrimer (i.e., the R group in FIG. 2 is already a chemical and/or biological sensory group). Thereafter, the diacetylene-functionalized dendrimer having the terminal sensory groups is exposed to gamma or ultraviolet irradiation to induce intramolecular cross-linking to form a reaction product comprising a dendrimer core, an outer layer comprising terminal sensory groups, and, located between the sensory groups and the dendrimer core, intramolecular segments containing alternating conjugated double and triple bonds. The intramolecular reaction of the diacetylene moieties (i.e., the diacetylene topochemical polymerization) is illustrated schematically in FIG. 1.

In FIG. 4, a dendrimer having x terminal amine groups is reacted with y diacetylene reagents and z reagents which do not contain diacetylene functional groups to form a dendrimer having y diacetylene moieties and z non-diacetylenic moieties that branch out radially from the dendrimer core. One or more $R_1$ and/or $R_2$ sensory groups can be attached to the diacetylenic and/or non-diacetylenic lipids prior to or subsequent to the reaction depicted in FIG. 4. The resulting chemical and/or biological sensor may not undergo intramolecular cross-linking and would in that case function as a photoluminescent sensor only.

An advantage of using a dendritic polymer core for the preparation of chemical and/or biological sensors of FIG. 3 is that it facilitates the intramolecular reactions of the diacetylene moieties described above and shown in the same figure, and allows preparation of water-soluble or oil-soluble products. The dendritic polymer core provides a temple that favors intramolecular reaction of the diacetylene moieties and prevent their intermolecular reactions (i.e., reactions between diacetylene moieties attached to different dendritic polymer molecules) because of steric constraints that the molecular architecture of dendritic polymers impose upon adjacent surface end groups. According to one current understanding of multi-arm star polymers, their intramolecular density is at the maximum at the point of arm attachment and decreases towards the periphery of the arms, and in good solvents for the arms, they stretch out in order to minimize repulsive interactions between the neighboring segments. Each of these effects aids in the dense packed alignment of the diacetylene functional groups and hence favors intramolecular topochemical polymerization, leading to the desired optically responsive behavior.

The spatial arrangement of the diacetylene moieties is strongly influenced by their position in the lipid chains as well as by the choice of dendrimer generation. Therefore, the length of the methylene spacers (shown in the diacetylene reagents of FIGS. 2 and 4) can be adjusted (e.g. varying parameters n and m) to promote intramolecular and suppress intermolecular polymerization of the diacetylene moieties. Because the mean separation between the arms in multi-arm star dendritic polymers increases with distance from the dendritic core, the diacetylene functional groups will be in optimally close proximity at small values of n (e.g., less than or equal to 5). Higher generation dendrimers and higher molecular weight dendritic polymers should, therefore, lead to higher steric constraints and to more closely packed diacetylene functional groups, further enhancing the probability of successful intramolecular topochemical polymerization. For these reasons, generation 4 and higher dendrimers, and other dendritic polymers having a weight average molecular weight in excess of 10,000 Daltons are preferred to minimize intermolecular cross-linking of the diacetylene moieties, and thereby provide soluble (e.g., water-soluble or hydrophobic organic solvent-soluble) macromolecular compounds and chemical and/or biological sensors in accordance with this invention. In addition, the use of sufficiently long methylene spacers after the diacetylene moieties should lead to enhanced steric repulsion between individual multi-arm star molecules preventing intermolecular reactions. Desirably, m is equal to or greater than 8 for the diacetylene reagent shown in FIGS. 2 and 4. Further enhancement of steric repulsion can also be achieved by using bulkier (i.e., larger) R groups.

In order to further favor intramolecular topochemical polymerization of the diacetylene moieties and prevent their intermolecular polymerization, the reaction is preferably carried out at high dilution (e.g., $10^{-5}$ M).

It is not necessary that all of the diacetylene moieties are intramolecularly polymerized in order to provide a highly colored and optically responsive material. For example, a soluble form of polydiacetylene with a degree of polymerization of about 2400 and an average conjugation length of only 6–7 units exhibits a yellow color when dissolved in chloroform (a good solvent) and a red color when the average conjugation length is increased to about 15 units and chloroform solution is titrated with hexane (a poor solvent). The conjugation length is defined as the number of carbon-carbon bonds over which conjugation of the backbone is maintained without interruption.

In accordance with an alternative path (b) of FIG. 3, the diacetylenic lipid is first attached to the terminal functional groups of the dendrimer core to form a diacetylene functionalized dendrimer which contains the terminal R groups or linker moieties that are subsequently converted into sensory groups. The product is then irradiated (such as with gamma or ultraviolet radiation) to cause topochemical polymerization of the diacetylenic moieties.

As another alternative, the colorimetric chemical and/or biological sensors of this invention can be prepared by path (c) of FIG. 3, wherein the R groups in FIGS. 2 and 3 are linker groups that are converted into sensory groups after the diacetylene-functionalized dendrimer product of FIG. 2 is irradiated to photopolymerize the diacetylene units.

Each of the three synthetic pathways shown in FIG. 3 depend on the use of orthogonal alpha,omega-substituents at the ends of the diacetylene lipid. The alpha-linking group will react exclusively with the terminal groups of the dendrimer, and the omega-linking groups will either be the sensory groups (path (a) of FIG. 3) or reactive groups that convert into the sensory groups (paths (b) and (c) of FIG. 3). For example, electrophilic N-hydroxysuccinimidyl ester is an appropriate choice for the alpha-linking group when using amine-terminated dendritic core reagents because it is very reactive toward aliphatic amines and much less reactive with water or alcohols. The omega-linking group could then be an alcohol or a substituted maleimide. The maleimide-linking group can further react with a mercapto-functionalized sensory group by Michael addition.

The examples shown in FIGS. 2, 3 and 4 are illustrative of techniques for preparing particular chemical and/or biological sensors of this invention. However, the invention is not limited to these particular examples only. As with attachment of the diacetylene monomers to the dendritic polymers, various known chemistries may be used for attachment of the sensory groups to the omega-linking groups of the diacetylene monomers, either before or after attachment of the diacetylene monomers to the dendritic polymer, and either before or after intramolecular reaction of the diacetylene moieties.

The choice of sensory groups will depend on the identity of the targeted chemical or biological analyte and on the type of binding desired (i.e., large verses small analyte; specific binding verses non-specific binding, etc.). The sensory groups of the present invention can be selected from a wide variety of moieties having an affinity for the analyte of choice, and may be of a broad range, such as when a class of materials is to be assayed.

ling the organization of matter at previously unattainable levels of the nanoscopic size scale (i.e., from about 1 to about 15 nanometers).

The structural precision of dendrimer molecules (defined by branching functionalities of the core cell and interior branch junctures) controls dendrimer molecule shape and size, as well as their uniformity (i.e., size distribution). As a consequence of pronounced synthetic control, dendrimers are highly monodisperse polymers which (particularly at higher generations) adopt almost ideally spherical shapes. Further, while the molecular weight of dendritic polymers may range from several thousand to a million, their molecular radii remain within the nanoscopic size range. Table 1 lists selected molecular properties of commercially available PAMAM and PPI dendrimers, including number of end-groups, molecular weight, and size.

TABLE 1

Selected Molecular Properties of Polyamidoamine (PAMAM) and Polypropyleneimine (PPI) Dendrimers.

| | PAMAM | | | PPI | | |
|---|---|---|---|---|---|---|
| Generation | Number of End-groups | Molecular Weight | $R_G/R_H$, Å | Number of End-groups | Molecular Weight | $R_G/R_H$, Å |
| 1 | 8 | 1430 | ~/10.1$^b$ | 8 | 773 | 6.9$^c$/9.2$^b$ |
| 2 | 16 | 3256 | ~/14.4$^b$ | 16 | 1687 | 9.3$^c$/12.1$^b$ |
| 3 | 32 | 6909 | 16.5$^c$/17.5$^b$ | 32 | 3514 | 11.6$^c$/15.4$^b$ |
| 4 | 64 | 14215 | 19.7$^c$/25$^b$ | 64 | 7168 | 13.9$^c$/19.8$^b$ |
| 5 | 128 | 28826 | 24.3$^c$/27.2$^a$ | | | |
| 6 | 256 | 58048 | 30.3$^c$/33.7$^a$ | | | |
| 7 | 512 | 116493 | 35.8$^c$/40.5$^a$ | | | |
| 8 | 1024 | 233383 | ~/48.5$^a$ | | | |
| 9 | 2048 | 467162 | 57$^a$/49.2$^c$ | | | |

$^a$Values from size exclusion chromatography (SEC) data obtained at 25° C. in 0.1 molar citric acid in water.
$^b$Values calculated from dilute solution viscometry (DSV).
$^c$Values obtained from small angle neutron scattering (SANS) data: for PAMAMs in the same solution as in a; for PPIs in D$_2$O.
$^d$R$_G$ and R$_H$ represent radius of gyration and hydrodynamic radius, respectively.

Examples of sensory groups that may be used include, but are not limited to, peptides, carbohydrates, nucleic acids, biotin, drugs, chromophores, antigens, chelating compounds, molecular recognition complexes, ionic groups, polymerizable groups, linker groups, electron donors, electron acceptors, hydrophobic groups, hydrophilic groups, receptor binding groups, antibodies, and other organic molecules which bind to receptors, as well as combinations thereof.

The dendritic polymer cores have unique properties that arise from their molecular architecture, which make them particularly useful as template precursors for calorimetric chemical and/or biological sensor molecules. Dendritic molecules, particularly dendrimers, are globular, highly branched, nanoscopic macromolecules having two or more tree-like dendrons that emanate from a central atom or atomic group. These dendrons are composed of branched cells which contain at least one branch juncture and which may be considered as branched analogs of repeat units in classical chain-type polymers. The branch cells represent the main building blocks of dendrimer molecules, and are organized around the central atom or atomic group in mathematically precise, geometrically regular concentric layers (called generations). Because of the unique architectural organization of dendrimers and other dendritic polymers, they provide unprecedented opportunities for control- As can be seen from Table 1, the number of dendrimer end-groups increases geometrically with generation. Thus, high generation dendrimers may possess hundreds of end-groups per molecule, and if these groups are reactive, dendrimers can be chemically modified to form a variety of different derivatives. In addition to this, because these groups are easily accessible (i.e., exo-presented), they are also available for interaction with the components of the external environment.

With their active, built-in optically responsive colorimetric or photoluminescent reporter functionality, the molecular chemical and/or biosensors of this invention represent a potentially major advancement over traditional assays which use passively labeled ligands. Additionally, the colorimetric chemical and/or biological sensors of this invention may utilize optical detection and measurement of analytes as opposed to more complex and costly detection methods such as fluorescence depolarization, fluorescence energy transfer, surface plasmon resonance and electrochemiluminescence, typically used with existing homogenous assays. A variety of different sensory interactions coupled with the same reporting functionality may be envisioned, so that the resulting products will not be a single case-specific biosensor, but rather an entire family of different variants. Examples of possible bioassay and/or biosensing applications include small molecule ligands such as haptens and large molecule ligands that participate in protein-protein interactions, nucleotide hybridization, receptor-virus interactions, etc., including both competitive and direct binding assays. Biotin, for example, could be conjugated to an alcohol linker at the end of the diacetylene lipid by means of carbodiimide induced coupling or to an amine linker by means of an N-hydroxysuccinimidyl ester. Histamine conjugation would involve reaction of a primary amine with an N-hydroxysuccinimidyl ester linker on the diacetylene lipid, while attachment of mercapto-functionality to dioxynivalenol would permit subsequent coupling to a maleimide linker.

As another specific example, a competitive hapten binding assay may be used to detect histamine and dioxynivalenol. In this type of assay, the small molecules function as both the analyte and a part of the sensory group. Following conjugation to the molecular sensor, the small molecules will be bound to antibodies such as anti-histamine or anti-dioxynivalenol, leading to an appropriate conformational/colorimetric response. Subsequent interaction with more small molecular analytes will displace some of the conjugated ligands from antibodies, leading to partial reversal of the conformational perturbation of the reporter units, as well as to the associated colorimetric response. A major advantage of this type of assay is that there is no need for separating bound ligand from free ligand since the extent of binding is measured from the optical characteristics of a homogeneous sensing ensemble.

Although an advantage of this invention relates to the provision of soluble chemical and/or biological molecular sensors that may, for example, be applied directly to a biological tissue sample or mixed with a liquid, whereby analytes may be detected and quantified by observable color changes of the molecular sensors, the molecular sensors of this invention may also be immobilized on a substrate if desired. Such substrates may include latex or glass beads, chemically functionalized particles (including chemically functionalized dendrimers or other dendritic polymers), or magnetic microparticles, which would be more suitable for immunoassay preparation and handling. Illustrative examples include detection of *E-coli* O157:H7 or salmonella with complementary conjugated antibodies bound to particulate substrates having a diameter of for example 1–5 microns.

When the dendritic polymer is a cross-linked network of dendritic polymer molecules, the cross-linked network may serve as a solid substrate or support. In this case the molecular sensor inherently includes a solid support on which the sensory groups are inmobilized.

The mechanism by which observable spectral changes occur as a result of binding between the sensory groups of the molecular sensors of this invention and analytes is not known with absolute certainty. However, most likely, the color changes are due to stresses induced by binding of an analyte to the sensory group which causes the effective conjugation lengths of alternating conjugated double and triple bond segments to change, which in turn results in an observable color change. This color change may be detected visually (i.e., with the unaided human eye) or with the aid of colorimetric instrumentation. Such instrumentation can be used to provide an accurate quantitative measurement of an analyte. Alternatively, binding of an analyte with one or more sensory groups would induce stresses which would change the photoluminescent properties of one or more diacetylene segments, which would be detected by fluorometric instrumentation.

Reaction of the dendritic polymer core with the diacetylene reagent may be conducted in a solvent in which both the dendritic polymer and the diacetylene reagent are soluble. For example, in the case of an amine-terminated PAMAM dendrimer reacted with a diacetylene monomer(s) as shown in FIGS. 2 and 4, a suitable solvent is a mixture of N-methylpyrrolidinone and tetrahydrofuran.

The solubility of the colorimetric macromolecules (with or without sensory groups) can be adjusted by appropriate selection of the dendritic polymer molecule, modification of the surface chemistry of the dendritic polymer molecule (either before or after attachment of the diacetylene reagent), and selection of the sensory group.

In addition to their use as molecular biochemical and/or chemical sensors when combined with sensory groups, the diacetylene modified dendritic polymers may also have utility as additives for plastic structural components. In particular, it is believed that the macromolecular compounds of this invention may be added to a polymeric blend to provide a component that changes color in response to mechanical forces imposed on the plastic component and/or in response to mechanical fatigue. Alternatively, a plastic containing the colorimetric macromolecules of this invention may be added to a coating composition applied to a substrate, such as metals or other structural materials. In this case, the additive may be useful for providing an observable color change when the structural material is subjected to mechanical forces and/or undergoes mechanical fatigue.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. A compound comprising:
   a dendritic polymer core; end
   chemical moieties covalently bonded to terminal groups of the dendritic polymer core, the chemical moieties being intramolecularly linked by alternating conjugated double and triple bonds.

2. The compound of claim 1, wherein the dendritic polymer is a dendrimer.

3. The compound of claim 1, wherein the dendritic polymer is a tecto-dendrimer.

4. The compound of claim 1, wherein the dendritic polymer is a dendron.

5. The compound of claim 1, wherein the dendritic polymer is a hyperbranched polymer.

6. The compound of claim 1, wherein the dendritic polymer is a hypercomb-branched polymer.

7. The compound of claim 1, wherein the dendritic polymer is a hyperbranched polymer having an average degree of branching of from about 0.25 to about 0.45.

\* \* \* \* \*